United States Patent [19]

Bredeweg et al.

[11] 4,238,450

[45] Dec. 9, 1980

[54] CRUCIBLE LOADING-UNLOADING SYSTEM

[75] Inventors: Roger L. Bredeweg, Stevensville; Edward P. Povilaitis, Coloma; Ramsey G. Reed, St. Joseph, all of Mich.

[73] Assignee: Leco Corporation

[21] Appl. No.: 13,031

[22] Filed: Feb. 21, 1979

[51] Int. Cl.³ ..................... G01N 31/12; G01N 33/00
[52] U.S. Cl. .................. 422/63; 23/230 PC; 422/65; 422/78
[58] Field of Search ............... 23/230 PC; 422/65, 63, 422/78, 80

[56] References Cited

U.S. PATENT DOCUMENTS

| | | | |
|---|---|---|---|
| 3,489,521 | 1/1970 | Buckle et al. | 422/65 |
| 3,511,613 | 5/1970 | Jones | 422/63 |
| 3,578,412 | 5/1971 | Martin | 422/65 |
| 3,635,394 | 1/1972 | Natelson | 422/65 X |
| 3,985,505 | 10/1976 | Bredeweg | 23/230 PC |

*Primary Examiner*—Barry S. Richman
*Attorney, Agent, or Firm*—Price, Heneveld, Huizenga & Cooper

[57] ABSTRACT

A system for stepwise advancing a row of crucibles individually through a loading station of an induction furnace includes a plurality of articulated fingers for gripping each of the crucibles. The fingers are mounted to a first slide for movement along the direction of advancement of the crucibles. The first slide is mounted to a second slide for advancing and retracting the fingers into crucible engaging and disengaging positions, respectively. Control means are provided for controlling the movement of the slides and the articulated fingers sequentially to stepwise advance the crucibles through the loading station.

23 Claims, 7 Drawing Figures

CRUCIBLE LOADING-UNLOADING SYSTEM

BACKGROUND OF THE INVENTION

The present invention relates to analyzers for the analysis of steel samples and particularly to a crucible loading and unloading mechanism for automatically moving crucibles into and out of an induction furnace of such an analyzer.

In analyzers used, for example, in the steel industry for determining the carbon and/or sulphur content of steel specimens, such as Model No. CS-46 commercially available from Leco Corporation of St. Joseph, Michigan, in the past it has been necessary to manually load the ceramic crucibles into the induction furnace. The induction furnace in turn heats the specimen within the ceramic crucible combusting it at temperatures of about 1700° C. to generate gases representative of the sulphur and/or carbon content of the specimen.

In many laboratories conducting such analysis, a great number of sample analyses are conducted during a day's operation. Once the analysis is completed, the expended crucibles are very hot and tongs are required to handle them. Such manual crucible loading and unloading process is time consuming, tedious, and slow.

It is frequently desirable to do several analyses in a particular sequence to ascertain changes in the carbon and/or sulphur content of a specimen as various steel manufacturing parameters are varied. If a manual loading system is employed, it is possible to mix up the specimen sequence and obtain erroneous results.

Some attempts have been made to provide automatic loading of crucibles into an induction furnace. Such efforts include the sliding of crucibles along a track into the induction station or providing a turntable in which crucibles are rotatably moved into the induction station. The analyzers in which the crucible loading and unloading mechanism is employed are relatively compact and, thus, require a compact crucible handling system. Such prior attempts to provide an automatic crucible handling system have not been usable, however, due in part to the complexity and bulk of their construction and their lack of reliability.

SUMMARY OF THE INVENTION

The present invention overcomes the deficiencies of the prior art by providing an automatic crucible loading and unloading system whereby crucibles can be aligned in a row on a ledge of the instrument and advanced in a stepwise fashion into and out of the induction station automatically. With such a system, several analyses can be run unattended once the ledge has been loaded with the crucibles. Since it is not necessary to manually handle the crucibles with tongs, this system is faster since it operates more rapidly than the crucibles can be handled manually.

Systems embodying the present invention include a plurality of articulated fingers for gripping each of the crucibles. The fingers are mounted to a first slide for movement along the direction of advancement of the crucibles and the first slide is mounted to a second slide for advancing and retracting the fingers into crucible engaging and disengaging positions. In the preferred embodiment of the invention, the fingers lift the crucibles as they are moved and then drop the crucibles once advanced. Control means are provided for controlling the movement of the slides and the articulated fingers to sequentially and stepwise advance the crucibles through the loading station.

These and other features, and objects of the present invention will become apparent upon reading the following description thereof together with the drawings in which:

DETAILED DESCRIPTION OF THE PREFERRED EMBODIMENT

Figure 1:
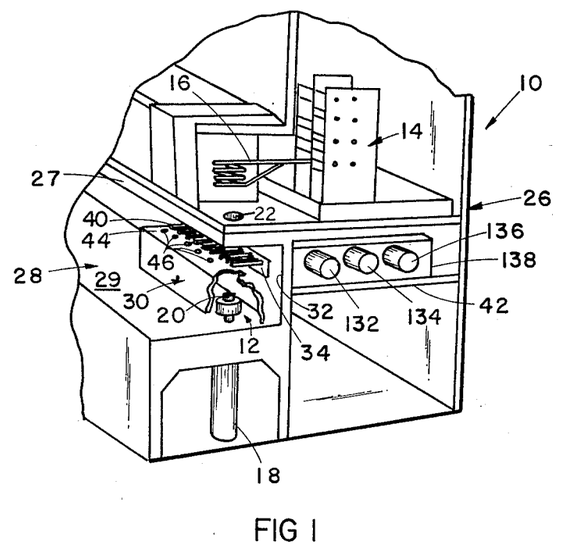
FIG. 1 is a fragmentary perspective view of an analyzer embodying the present invention.

Referring initially to FIG. 1, there is shown an analyzer 10 incorporating the present invention and which includes a crucible loading station 12 associated with an induction furnace 14. Furnace 14 includes an induction heating coil 16 into which a ceramic crucible which can be of the type disclosed in U.S. Pat. No. 3,100,155, issued Aug. 6, 1963, to H. C. Wagner, and assigned to the present assignee is positioned. The crucible is positioned axially within the center of the induction coil 16 by means of a cylinder 18 which raises and lowers a ceramic cylindrical pedestal 20 also shown in FIG. 4 through the crucible loading and unloading mechanism generally designated as 30 in FIG. 1 and through an aperture 22 in the floor of the induction furnace.

Instrument 10 includes a suitable cabinet 26 housing the induction furnace 14 and the crucible handling system 30 and an associated analyzer which forms no part of the present invention. The analyzer, for example, can be of the type represented by Model No. CS-46 noted earlier. The instrument includes a generally open front 28 defining a surface 29 for supporting the crucible loading and unloading system. A vertical rear wall 32 includes a horizontally extending elongated slot 34 through which a plurality of spaced articulated finger pairs 40 extend over a ledge 44 on which the crucibles 15 are positioned as described in greater detail below. The crucible loading and unloading system 30 includes a base plate 42 on which the various components are supported and which in turn is suitably mounted to the instrument cabinet 26. Crucibles aligned in a row on ledge 44 are sequentially advanced in a stepwise fashion into alignment with the pedestal 20 which is then raised through aperture 22 raising the crucible and specimen therein within the induction coil 16. The induction coil is then actuated to heat the specimen material within the crucible to a temperature of approximately 1700° C. combusting the solid specimen into its gaseous components which are then transferred to the analyzer. One combustion and analyzer system which can be used in analyzer 10 is disclosed in U.S. Pat. No. 3,985,505, issued Oct. 12, 1976, to R. Bredeweg, and assigned to the present assignee, the disclosure of which is incorporated herein by reference.

Ledge 44 is spaced vertically below the floor 27 of the induction furnace and analyzer a distance sufficient to permit the instrument operator to position a row of crucibles on the indexing recesses 46 formed along the ledge in predetermined spaced relationship. Finger pairs 40 are then moved forwardly to grip the crucibles, advance them in a stepwise fashion so the endmost crucible advances into the loading station 12 for positioning a crucible on pedestal 20. The fingers are retracted during the combustion portion of the cycle of operation and then moved in an opposite direction and advanced to grip and advance the next crucibles in the row lifting them from the ledge and advancing them into the loading station. Having briefly described the instrument and induction furnace to which the present invention pertains, a detailed description of the crucible loading and unloading system 30 of the present invention is now presented.

Figure 2:
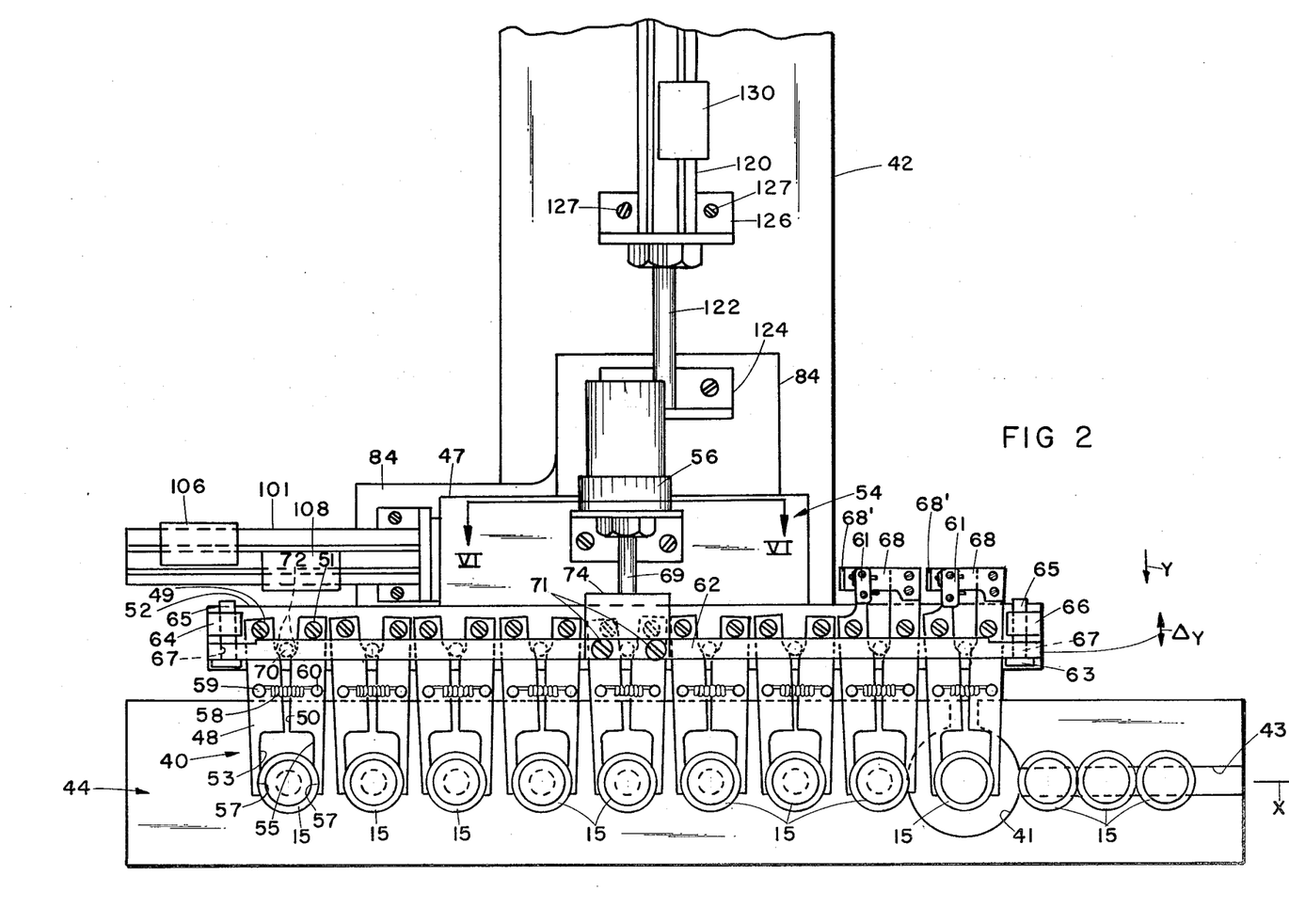
FIG. 2 is an enlarged fragmentary plan view of the crucible loading and unloading mechanism of the present invention.
Figure 3:
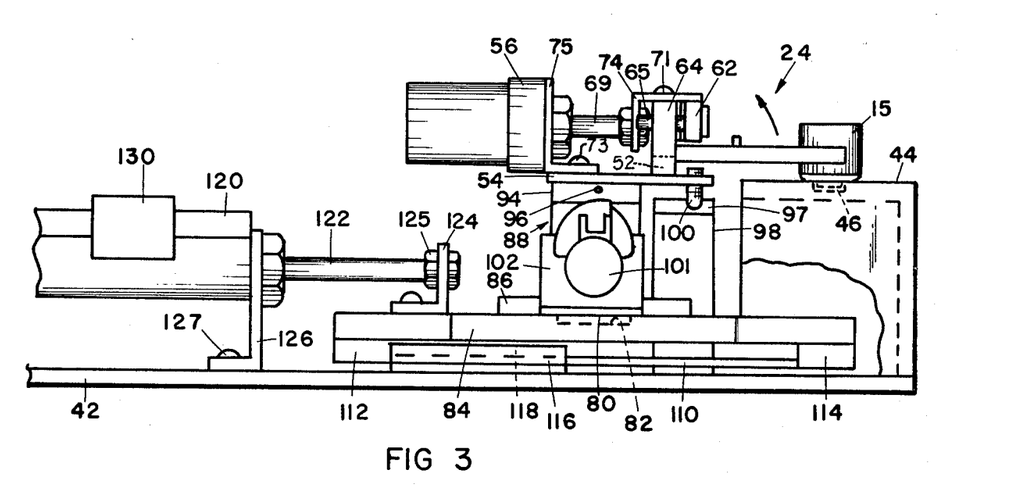
FIG. 3 is a fragmentary left side elevational view of the structure shown in FIG. 2.

Referring initially to FIGS. 2 and 3, each of the finger pairs 40 are of substantially identical construction so that only a single finger pair will be described in detail. The finger pairs 40 form part of a finger subassembly 24 (FIG. 3) which is positioned above the means for actuating the fingers which includes first and second slide assemblies. Each finger pair of the nine such pairs of the preferred embodiment include a first finger 48 (FIG. 2) and a second finger 50 pivotally mounted at a rear end by means of pivot posts 49 and 51, respectively, to a spacer block 52 which in turn is mounted to a finger support plate 54. As seen in FIG. 2, the support plate 54 is generally T-shaped having the cross of the T extending with width of the spaced finger pairs 40 and a rearwardly extending shortened leg 47 to which cam actuating means comprising a pneumatic cylinder 56 is secured for actuating the fingers as described in greater detail below.

Each of the fingers 48 and 50 extend forwardly from the pivot points 49 and 51 with the rear portion of the legs being spaced apart and the front portion of the legs configured with a recess 53 and 55, respectively, to form a crucible receiving opening. The tips of the fingers 48 and 50 are also semicircularly recessed at 57 to engage the generally cylindrical sidewalls of the crucible approximately midway through the height of the crucible as shown also in FIG. 4. The fingers are freely pivoted about pins 49 and 51 and are biased in a normally closed position by a bias tension spring 58 extending between a fixed post 59 which extends upwardly from finger 48 and a fixed post 60 which extends upwardly from finger 50. Spring 58 is tensioned between these posts which are located approximately midway between the front and rear of the fingers to hold the fingers together with sufficient pressure for holding the ceramic crucible and its contents.

The finger pairs 40 are simultaneously opened and closed by a cam means comprising a movable actuating bar 62 extending the width of the finger assembly 24 and slidably mounted to opposite ends of the finger support plate 54 by means of a pair of mounting bosses 64 and 66 and sliding pins 65 mounted to the bosses 64 and 66 and extend outwardly therefrom. Bar 62 includes an aperture 67 through each end and a linear bearing 63 slidably couples bar 62 to the pins 65 at opposite ends permitting the bars to move in a direction indicated by arrow ΔY in FIG. 2 with respect to the plate 54. Bar 62 includes a plurality of spaced downwardly depending camming rods 70 which fit between the fingers 48 and 50 of each finger pair 40 and are spaced to and have a diameter such that as the bar 62 is moved forwardly (downwardly in FIG. 2) the cylindrical rods 70 engage the inner facing surfaces of fingers 48 and 50 opening the fingers to release the crucibles.

To enhance this camming action, the fingers include opposed facing curved camming surfaces 72 cooperating with the rods 70 to provide the desired amount of excursion of the ends of the fingers for a relatively small motion of bar 62. The surfaces 72 thus are curved in the preferred embodiment to provide a fast acting camming action between bar 62 and fingers 48 and 50. In the preferred embodiment, for example, for a motion ΔY of ⅛ of an inch of rod 62 with respect to the fingers, the fingers open ⅜ of an inch. The crucible diameter is 31/32 of an inch and when the fingers are in their fully opened position, there is an opening between the fingers of 1.625 of an inch. The fingers are moved forwardly when in this open position such that tips 57 clear the sidewalls of the crucible whereupon the bar 62 is retracted rearwardly and the crucibles are held with the tension of spring 58 as shown in FIG. 2.

Bar 62 is moved with respect to the support plate 54 by means of cylinder 56 having a shaft 69 coupled to an L-shaped bracket 74 coupling the end of shaft 69 to the bar 62 by conventional fastening means such as screws 71. Cylinder 56 in turn is mounted to the base support plate 54 by means of a second L-shaped bracket 75 secured to plate 54 by means of fastening screws 73. Mounted to the endmost pairs of fingers on the right end as seen in FIG. 2, are a couple of detectors and means for actuating the detectors. The detectors comprise switches 61 while the actuators comprise L-shaped brackets 68 which actuate the switches 61 to provide an electrical control signal indicating whether or not a crucible is in position to be gripped by the two pairs of fingers 40 on which these switches are mounted. Thus, if a crucible is not present, the switch will provide a signal indicating the absence of such a crucible. As described in greater detail below, these signals are employed for stopping the system in the event a crucible is either not present for loading into the loading station or gets hung up in the induction furnace and thereby requires manual removal. The switches are actuated by a vertically extending tab portion 68' of the legs which engage the switch button associated with each of the switches.

Having described the finger actuating mechanism for opening and closing the fingers, a description of the mechanism for advancing the fingers along the line of travel of the crucibles into the loading station 12 in the direction of arrow X in FIG. 2 follows.

Figure 6:
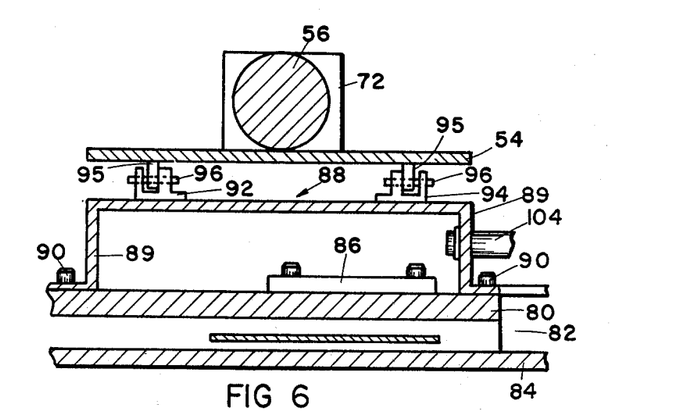
FIG. 6 is a fragmentary cross-sectional view taken along section line VI—VI in FIG. 2.

The support plate 54 for the finger subassembly 24 is mounted to a first slide assembly comprising a rectangular slide member 80 mounted in a correspondingly shaped rectangular slot 82 in plate 84 (FIGS. 3 and 6). A retainer plate 86 holds the slide 80 in position and a generally U-shaped bracket 88 has downwardly depending legs 89 secured to slide 80 by means of fastening screws 90 as best seen in FIG. 6.

Plate 54 and the structure mounted thereto is pivotally mounted to the bracket 88 by means of a pair of U-shaped mounting bosses 92 and 94 (FIG. 6) by means of downwardly depending legs 95 mounted to the plate and pivotally mounted between the vertical shoulders of the U-shaped mounting brackets 92 and 94 by means of pivot pins 96. The purpose of this pivot connection between the plate 54 and slide bracket 88 is to permit the fingers 40 mounted to the plate to be raised and lowered as the slide 80 is moved in a direction indicated by arrow X in FIG. 2 by means of the cam mechanism shown in FIG. 4.

Figure 4:
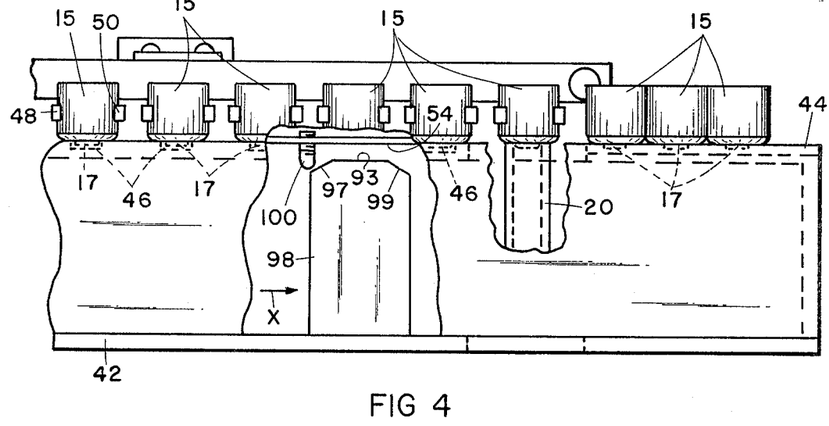
FIG. 4 is a fragmentary partly broken away front elevational view of the structure shown in FIGS. 2 and 3.

The cam mechanism shown in FIG. 4 comprises a cam plate 98 mounted to base plate 42 and including a leading edge 97 inclined upwardly in the direction of arrow X and a trailing edge 99 inclined downwardly in the direction of arrow X. Between these edges is a flat cam surface 93. A cam follower pin 100 is threadably secured to plate 54 and has a rounded surface engaging surface 97 pivoting the plate 54 upwardly thereby lifting the fingers and crucibles held there by crucibles from the circular recesses 46 and off the surface of ledge 44 as slide 80 is moved to the right in FIG. 2 in the direction indicated by arrow X. The cam follower 100 engages the surface 93 retaining the elevated position of the crucibles until the crucibles have been advanced an incremental distance corresponding to slightly less than the spacing between adjacent recesses 46 whereupon the cam follower rides down inclined surface 99 lowering the crucibles into the next adjacent position along the ledge 44 with the leading crucible being positioned in the loading station. As seen in FIGS. 1, 2, and 4, the ledge 44 for receiving the crucibles 15 comprises a cast rectangular housing having, as best seen in FIG. 2, a circular opening 41 at the loading station permitting the pedestal 22 to extend through the ledge and carry a crucible into the induction furnace. The circular recesses 46 are spaced approximately 1.625 inches from center to center and cooperate with the downwardly projecting buttons 17 (FIG. 4) on the crucibles 15 for indexing the crucibles and spacing them for movement along the ledge into the loading station. A rectangular slot 43 is provided at the exit end (to the right in FIG. 2) of the loading station such that the crucibles, once used, will slide off of the ledge into a suitable receptacle which can be placed at the right end.

Slide 80 which provides the motion along the ledge for the crucibles is actuated by means of a cylinder 101 (FIGS. 2 and 3) which is stationarily mounted at one end to plate 84 by means of a bracket 102. The shaft 104 of the cylinder 101 is coupled to slide 80 through leg 89 of the U-shaped bracket 88 as best seen in FIG. 6. Associated with cylinder 101 is a pair of detectors 106 and 108 (FIGS. 2 and 7) which provide motion limit signals such that the cylinder can be actuated and controlled for movement of the desired 1½ inch stroke. Having described the mechanism for elevating the fingers for lifting the crucibles off of the ledge and for advancing them in a stepwise fashion along the ledge, a description of the mechanism for advancing and retracting the finger subassembly 24 is now presented in conjunction with FIGS. 2 and 3.

As noted earlier, the fingers 40 retract within the slot 34 in the front wall 32 of the instrument and are moved in a direction opposite direction X and then advanced into a crucible gripping position for purposes of stepwise advancing the crucibles. In order to achieve the retraction and advancement of the crucible subassembly 24 in a direction indicated by arrow Y in FIG. 2, a second slide assembly is employed. The first slide assembly plate 84 is also mounted to the second slide assembly so that the first slide assembly and finger subassembly 24 move with the second slide assembly.

The second slide assembly comprises a slide member 110 as best seen in FIG. 3 mounted in spaced relationship below member 84 by means of a pair of spaced end spacer blocks 112 and 114. Slide 110 extends through a rectangular slot 118 defining a guide in mounting plate 116 for the slide 110. Plate 116 in turn is mounted to the base plate 42 by means of recessed screws (not shown) so as not to interfere with the motion of slide 80. Slide 110 is moved by a pneumatic cylinder 120 having a shaft 122 coupled to member 84 by means of an L-shaped bracket 124 and suitable nuts 125. The cylinder 120 in turn is mounted to plate 42 by means of an L-shaped bracket 126 by suitable fastening screws 127. Cylinder 122 also includes detection means 130 for indicating the travel limits of the slide which in the preferred embodiment was approximately 1½ inches which was sufficient to assure the leading edges of fingers 48 and 50 of each of the finger pairs 40 cleared the crucibles when the finger subassembly is being returned to its starting position in a direction opposite arrow X in FIG. 2. The slides and corresponding guide plates in the preferred embodiment are made of a lubricous polymeric material such as Delrin ® to facilitate motion of the elements.

Figure 7:
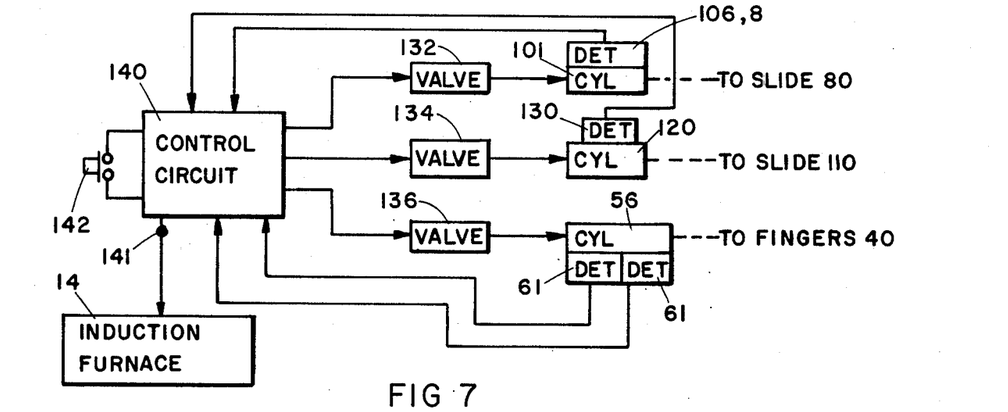
FIG. 7 is a circuit diagram partly in block and schematic form of a control system for the present invention.

In order to control the cylinders 56, 101, and 120, three electrically actuated pneumatic control valves 132, 134, and 136 (FIGS. 1 and 7) are employed and are mounted to a plenum 138 (FIG. 1) for supplying pneumatic pressure to the cylinders through the valves. The electrically actuated valves in turn are actuated by signals from a control circuit 140 (FIG. 7). The control circuit 140 includes suitable logic circuits for cycling the valves 132, 134, and 136 and the associated cylinders in a conventional manner through a cycle of operation to achieve the stepwise advancement of crucibles. Circuit 140 is of generally conventional design for achieving this purpose and includes a control output terminal 141 for applying a control signal to the induction furnace 14 for activating the RF coil 16 associated with the furnace. To initiate a cycle of operation, an operator actuated push button 142 is provided. The control circuit 140 receives input signals in a closed loop feedback coupling from the detectors 61, 106, 108, and 130 which indicate when one portion of the cycle has been completed and the next successive portion of the cycle is to be initiated. A cycle of operation of the crucible handling system is now described in conjunction with FIG. 5 which is a graphic illustration representing the rectilinear pattern of motion of the finger pairs 40 through a cycle of operation.

OPERATION

Figure 5:
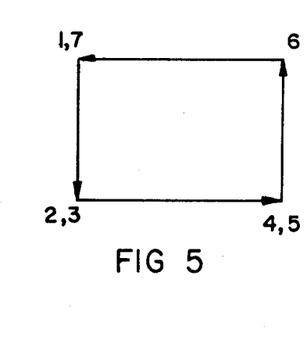
FIG. 5 is a schematic diagram of a cycle of operation of the system of the present invention.

Referring now to the FIGS. including FIG. 5, a cycle of operation is initiated at point 1 shown in FIG. 5 in which the finger subassembly is in its rearward position with cylinder 120 retracting slide 110 rearwardly (to the left in FIG. 3) and with cylinder 101 actuated to retract slide 80 to the left shown in FIG. 2. In this initial position, fingers 40 are in the open position by the actuation of cylinder 56 and the fingers are retracted to some extent within slot 34 (FIG. 1). The operator positions the number of crucibles including samples for analysis on the recesses 46 on ledge 44 with the first specimen being positioned in the recess 46 immediate to the left (FIG. 2) of the aperture 41. This then will become the first crucible which is introduced to the induction furnace by the crucible loading mechanism. Upon actuation of the start switch 142 (FIG. 7) cylinder 120 is actuated to advance slide 110 and the finger subassembly forwardly to position 2 shown in FIG. 5. Next, the fingers are closed by the actuation of valve 56 to move bar 62 rearwardly such that the cam rods 70 move rearwardly allowing the fingers 48 and 50 of each finger pair to close against the sidewalls of the crucibles in the position shown in FIG. 2. This step is indicated by reference numeral 3 in the diagram of FIG. 5.

Next, cylinder 101 is actuated to move slide 80 to the right as shown by arrow X in FIG. 2 which through the camming mechanism 98, 100 lifts the crucibles out of recesses 46, holds them in an elevated position as they are moved to the right and subsequently lowers the crucibles in the next successive recess to the right in FIG. 2 with the forwardmost crucible now being positioned by the rightmost pair of fingers 40 in FIG. 2 on the ceramic pedestal 20 as shown in FIG. 4. This step is indicated by the line extending between position 3 and 4 in FIG. 5. Cylinder 56 is then actuated to open the fingers as indicated by step 5 to release the crucibles in their stepwise advanced position.

Next, as indicated by step 6 in FIG. 5, the cylinder 120 is actuated to retract the finger assembly 24 by moving slide 110 to the left as shown in FIG. 3. The induction furnace is then actuated to raise pedestal 20 and the crucible 15 thereon into the induction coil 16 whereupon the normal furnace controls are employed together with the analyzer controls to combust the specimen and analyze the gaseous content thereof. Upon completion of the analysis, cylinder 101 is actuated to move the slide 80 to the left as shown in FIG. 2 moving the finger subassembly to the initial starting position 7 shown in FIG. 5. Switches 61 associated with the pair of fingers adjacent the rightmost end of the pair of fingers as shown in FIG. 2 provide control signals to logic circuit 140 such that in the event a crucible is not present in the recess 46 adjacent opening 41, the analyzer is deactivated so that pedestal 20 will not raise and the induction furnace 14 will not be actuated.

Subsequent to the analysis, the cycle is repeated with the pedestal 20 being lowered such that the now expended crucible on the pedestal is in position to be gripped by the rightmost pair of fingers as seen in FIG. 2. If the crucible is not present in the event that it becomes jammed in the induction furnace for any reason, switch 61 associated with the rightmost pair of fingers will provide a control signal deactivating the automatic crucible loading and unloading mechanism until the crucible can be manually freed. Although this is infrequent, it is desirable to assure that a successive crucible is not fed to the induction station of a previously introduced crucible is in a position where damage could occur to the induction coil or the furnace. As the loading and unloading mechanism cycles through subsequent cycles, the crucibles are lifted off of pedestal 20 and advanced to the slot 43 (FIG. 2) where they are slid along so that the endmost one will drop off into a suitable disposal receptacle.

In place of generally rectangular slide means for moving the finger assembly, the slide means may be rods with linear bearings slidably mounted thereon and to which the finger assembly is mounted. The cam means employed for raising and lowering the fingers may employ a roller follower instead of the nose pin 100. Further, the cam rods 70 may, in order to conserve vertical space, extend inwardly between the finger pairs from the rear instead of the top by mounting the actuator bar and rods at the rear of the fingers instead of above the fingers as shown.

The system of the present invention thereby provides an automatic sequentially operated means for advancing a series of spaced crucibles positioned at indexed locations along a ledge into a loading station for analysis and subsequent removal from the loading station for disposal. The invention, however, contemplates the use of a fewer or a greater number of fingers for loading one or more crucibles into the loading station and although one embodiment of the preferred embodiment has been particularly described herein, it will become apparent to those skilled in the art that various modifications to the preferred embodiment can be made by those skilled in the art without departing from the spirit or scope of the invention as defined by the appended claims.

The embodiments of the invention in which an exclusive property or privilege is claimed are defined as follows.

1. A system for mechanically advancing a series of crucibles into a loading station of an analyzer in a predetermined sequence for the analysis of specimens contained by the crucibles comprising:
   a crucible support surface positioned adjacent to the loading station for holding a series of crucibles in predetermined spaced relationship to one another;
   a plurality of lineally spaced crucible gripping fingers for alternately gripping and releasing said series of crucibles; and
   means for actuating said crucible gripping finger to stepwise and sequentially lineally advance said series of crucibles into the loading station in a predetermined sequence.

2. A system for automatically advancing a series of crucibles into a loading station of an analyzer in a predetermined sequence for the analysis of specimens contained by the crucibles comprising:
   a crucible support surface positioned adjacent to the loading station for holding a series of crucibles wherein said support surface includes means for spacing said crucibles in a row with a predetermined spacing between adjacent crucibles and wherein said support surface extends generally horizontally and said spacing means comprises a plurality of recesses formed downwardly in said support surface in spaced relationship to establish said predetermined spacing between adjacent crucibles, said recesses shaped to cooperate with the bottom of the crucibles for holding the crucibles in the spaced relationship;
   a plurality of spaced crucible gripping fingers for alternately gripping and releasing said series of crucibles; and
   means for actuating said crucible gripping fingers to automatically stepwise and sequentially advance said series of crucibles into the loading station.

3. The system as defined in claim 2 wherein said means for actuating said fingers includes means for opening and closing said fingers to permit said fingers to receive and grip a crucible respectively, first means for sequentially moving said fingers toward the loading station in a direction along a first axis of motion and away from the loading station in a direction parallel to and spaced from said first axis, and second means for moving said fingers toward the loading station in a direction along a second axis of motion and away from the loading station in a direction parallel to and spaced from said second axis.

4. The system as defined in claim 3 wherein said fingers comprise a plurality of finger pair assemblies mounted in spaced relationship along finger support means, each such assembly comprising a first finger pivotally mounted at one end to said finger support means, a second finger pivotally mounted at one end to said finger support means, biasing means coupled between said first and second fingers for urging said fingers toward one another to grip a crucible, and cam means positioned between said fingers and cam actuating means for actuating said cam means for urging said fingers apart into an open position for receiving or releasing a crucible.

5. The system as defined in claim 4 wherein said first and second fingers have curved surfaces formed to cooperatively engage a crucible, said curved surfaces positioned in opposed facing relationship at the end of said fingers remote from their pivotal coupling to said support bar.

6. The system as defined in claim 5 wherein said cam means comprises a plurality of rods mounted in spaced relationship along an actuator bar, said actuator bar mounted in movable relationship to said finger support means with said rods extending between said fingers of said finger pairs.

7. The system as defined in claim 6 wherein said first and second fingers each include a curved camming surface engaging one of said rods for opening said fingers in response to the movement of said actuating bar.

8. The system as defined in claim 7 wherein said cam actuating means for actuating said cam means comprises a cylinder having a shaft coupled to said actuating bar to move said bar for simultaneously opening or closing all of said fingers.

9. The system as defined in claim 8 wherein said means for moving said fingers in a direction parallel to a first axis of motion comprises a first base member, a first slide member positioned in slidable relationship on said first base member for motion in parallel relationship to said first axis of motion, means for mounting said support means for said finger pair assemblies to said first slide, and means for moving said first slide in opposite directions along said first base member.

10. The system as defined in claim 9 wherein said means for moving said fingers in a direction parallel to said second axis of motion comprises a mounting member, a second slide movably positioned on said mounting member for movement in a direction parallel to said second axis of motion, means for moving said second slide in opposite directions, and means for mounting said first base member to said second slide.

11. The system as defined in claim 10 wherein said means for coupling said finger support means to said first slide includes pivot coupling means between said first slide and said finger support means for permitting said fingers to raise and lower to lift and drop said crucibles from and to said crucible support surface, and cam means cooperating between said finger support means and said mounting means for raising and lowering said finger support means and said fingers thereon as said fingers are moved by said first slide in a direction parallel to said first axis of motion.

12. The system as defined in claim 11 wherein said cam means comprises a cam plate with a leading upwardly inclined camming surface, a generally flat middle camming surface and a trailing downwardly inclined camming surface, a cam follower positioned on said finger support means for engaging said camming surfaces, said cam plate coupled to said mounting means such that as said fingers are advanced toward the loading station they are raised, and said fingers are subsequently lowered as the endmost crucible approaches the loading station.

13. The system as defined in claim 12 and further including control means for sequentially actuating all of said cylinders to move said fingers in a direction parallel to said second axis into position to grip said crucibles, to close said fingers to grip said crucibles, to lift and advance said crucibles an incremental distance along said first axis toward said loading station with an endmost crucible being positioned at the loading station, to open said fingers to release said crucibles, to retract said fingers along the second axis away from the loading station, and to move said fingers along said first axis in a direction away from said loading station to complete a cycle of operation.

14. The system as defined in claim 13 wherein the endmost finger pair closest to the loading station includes detector means for providing an output control signal indicating the presence or absence of a crucible within said endmost finger pair.

15. The system as defined in claim 14 wherein the finger pair adjacent said endmost finger pair includes further detector means for providing an output control signal indicating the presence or absence of a crucible within said finger pair adjacent said endmost finger pair.

16. A system for mechanically moving a crucible into a loading station of an analyzer for the analysis of a specimen contained by the crucible comprising:
   stationary crucible support means positioned adjacent the loading station for holding a series of crucibles in predetermined spaced relationship;
   articulated finger means mounted to slide means and means for closing and opening said finger means to alternately hold and release a crucible; and
   means for lineally moving said slide means to sequentially advance crucibles held by said finger means from said crucible support means to the loading station.

17. The system as defined in claim 16 wherein said finger means are pivotally coupled to said slide means and further including cam means cooperating with said slide means for pivoting and thereby elevating said finger means to lift the crucible from said crucible support means as said crucible is carried between said crucible support means and the loading station.

18. The system as defined in claim 17 and further including a furnace and a vertically movable crucible receiving pedestal wherein the loading station includes an aperture formed in the crucible support means and wherein said aperture is aligned with said vertically movable crucible receiving pedestal for receiving a crucible from said finger means and moving the crucible into said furnace.

19. The system as defined in claim 18 and further including a base and second slide means movably positioned on said base for movement in a direction orthogonal to said first slide means, and wherein said first slide means is movably positioned on said second slide means.

20. A system for automatically moving a crucible into a loading station of an analyzer for the analysis of a specimen contained by the crucible comprising:
   crucible support means positioned adjacent the loading station;
   articulated finger means mounted to slide means and means for closing and opening said finger means to alternately hold and release a crucible wherein said finger means are pivotally coupled to said slide means and further including cam means cooperating with said slide means for pivoting and thereby elevating said finger means as said crucible is carried between said crucible support means and the loading station;

means for moving said slide means to carry a crucible held by said finger means from said crucible support means to the loading station;

a furnace and a vertically movable crucible receiving pedestal wherein the loading station includes an aperture formed in the crucible support means and wherein said aperture is aligned with said vertically movable crucible receiving pedestal for receiving a crucible from said finger means and moving the crucible into said furnace;

a base and second slide means movably positioned on said base for movement in a direction orthogonal to said first slide means, and wherein said first slide means is movably positioned on said second slide means; and means for actuating said first and second slide means alternately to define a rectangular path of motion of said finger means to stepwise advance a crucible into the loading station.

21. The system as defined in claim 20 wherein said crucible support means includes a plurality of crucible receiving positions and wherein said finger means comprise a plurality of pairs of fingers for sequentially stepwise advancing a row of crucibles into the loading station.

22. A system for mechanically moving a series of crucibles into a loading station of an analyzer in a predetermined sequence for the analysis of a specimen contained by the crucibles comprising:

crucible support means positioned adjacent the loading station;

first slide means;

lineally spaced finger means adapted to simultaneously carry crucibles, said finger means mounted to said first slide means;

means for moving said first slide means to carry crucibles held by said finger means from said crucible support toward the loading station;

a base;

second slide means movably positioned on said base and wherein said first slide means in slidably mounted to said second slide means and said second slide means is movable in a direction different than the direction of movement of said first slide means; and means for moving said first and second slide means in a predetermined pattern to sequentially lineally stepwise advance crucibles from said crucible support means to the loading station in a predetermined sequence.

23. A system for sequentially moving a series of crucibles into a loading station of an analyzer for the analysis of a specimen contained by the crucibles comprising:

crucible support means positioned adjacent the loading station;

first slide means;

finger means adapted to carry crucibles, said finger means mounted to said first slide means;

means for moving said first slide means to carry crucibles held by said finger means from said crucible support means to the loading station;

a base;

second slide means movably positioned on said base and wherein said first slide means is slidably mounted to said second slide means and said second slide means is movable in a direction different than the direction of movement of said first slide means; and means for moving said first and second slide means to sequentially stepwise advance crucibles from said crucible support means to the loading station; wherein said finger means are pivotally coupled to said first slide means and further including cam means cooperating with said first slide means for pivoting and thereby elevating said finger means as crucibles are carried between said crucible support means and the loading station by said finger means.

* * * * *

UNITED STATES PATENT AND TRADEMARK OFFICE
CERTIFICATE OF CORRECTION

PATENT NO. : 4,238,450
DATED : December 9, 1980
INVENTOR(S) : Roger L. Bredeweg

It is certified that error appears in the above—identified patent and that said Letters Patent is hereby corrected as shown below:

Column 2, line 3:

After "features" insert --advantages--

Column 12, line 3, Claim 22:

After "support" insert --means--

Column 12, line 6, Claim 22

"in" should be --is--

Column 12, lines 12 and 13, Claim 22

"lineally stepwise" should be --stepwise lineally--

Signed and Sealed this

Fourteenth Day of July 1981

[SEAL]

Attest:

Attesting Officer

GERALD J. MOSSINGHOFF
Commissioner of Patents and Trademarks